United States Patent
Black et al.

(10) Patent No.: US 10,845,517 B2
(45) Date of Patent: Nov. 24, 2020

(54) FILTER FOR LASER PROTECTION

(71) Applicant: BAE Systems plc, London (GB)

(72) Inventors: Daniel Benjamin Black, Chelmsford (GB); Leslie Charles Laycock, Chelmsford (GB)

(73) Assignee: BAE Systems plc, London (GB)

( * ) Notice: Subject to any disclaimer, the term of this patent is extended or adjusted under 35 U.S.C. 154(b) by 56 days.

(21) Appl. No.: 16/087,140

(22) PCT Filed: Mar. 20, 2017

(86) PCT No.: PCT/GB2017/050766
§ 371 (c)(1),
(2) Date: Sep. 21, 2018

(87) PCT Pub. No.: WO2017/163033
PCT Pub. Date: Sep. 28, 2017

(65) Prior Publication Data
US 2019/0129077 A1    May 2, 2019

(30) Foreign Application Priority Data

Mar. 24, 2016 (GB) .................................. 1604995.9
Nov. 23, 2016 (GB) .................................. 1619765.9

(51) Int. Cl.
  *G02B 5/20* (2006.01)
  *G02C 7/10* (2006.01)
  (Continued)

(52) U.S. Cl.
  CPC .............. *G02B 5/203* (2013.01); *A61F 9/022* (2013.01); *B64C 1/1476* (2013.01);
  (Continued)

(58) Field of Classification Search
  CPC .......... A61F 9/022; A61F 9/065; G02B 5/20; G02B 5/28; G02B 5/285; G02C 7/104
  See application file for complete search history.

(56) References Cited

U.S. PATENT DOCUMENTS 4,786,125 A  *  11/1988  Magarinos  ............... A61F 9/022
                                                     351/44
4,879,167 A     11/1989  Chang
                        (Continued)

FOREIGN PATENT DOCUMENTS

CN    101758227 A1   6/2010
EP    2602655 A1    12/2013
        (Continued)

OTHER PUBLICATIONS

International Preliminary Report on Patentability for Appl No. PCT/GB2017/050740 dated Sep. 25, 2018, 9 pages.
(Continued)

*Primary Examiner* — Cara E Rakowski
(74) *Attorney, Agent, or Firm* — Maine Cernota & Rardin (57) ABSTRACT

A method of forming a filter, comprising the steps of: —selecting at least a first wavelength corresponding to a predetermined laser threat and having a first colour in the visible spectrum; —providing a generally transparent substrate and forming a first notch filter region therein configured to substantially block incident radiation thereon of wavelengths within a first predetermined wavelength band including said first wavelength; —selecting a second wavelength having a second colour in the visible spectrum and forming a colour balancing notch filter region in said substrate configured to block incident radiation thereon of wavelengths within a wavelength band including said sec-
(Continued)

ond wavelength, thereby to balance or neutralise any colour distortion of said substrate caused by said first notch filter region.

14 Claims, 3 Drawing Sheets

(51) Int. Cl.

| | | |
|---|---|---|
| *G02B 5/28* | (2006.01) | |
| *A61F 9/02* | (2006.01) | |
| *B64C 1/14* | (2006.01) | |
| *E06B 3/67* | (2006.01) | |
| *E06B 5/18* | (2006.01) | |
| *G03H 1/04* | (2006.01) | |
| *G03F 7/00* | (2006.01) | |
| *A61F 9/06* | (2006.01) | |
| *B60J 3/00* | (2006.01) | |

(52) U.S. Cl.
CPC .......... *B64C 1/1492* (2013.01); *E06B 3/6715* (2013.01); *E06B 5/18* (2013.01); *G02B 5/20* (2013.01); *G02B 5/28* (2013.01); *G02B 5/285* (2013.01); *G02C 7/10* (2013.01); *G02C 7/104* (2013.01); *G03H 1/0402* (2013.01); *A61F 9/065* (2013.01); *B60J 3/00* (2013.01); *B64C 1/14* (2013.01); *G03F 7/001* (2013.01); *G03H 2001/0413* (2013.01); *G03H 2001/0439* (2013.01); *G03H 2223/17* (2013.01); *G03H 2223/24* (2013.01); *G03H 2260/12* (2013.01)

(56) References Cited

U.S. PATENT DOCUMENTS

| | | | |
|---|---|---|---|
| 4,963,471 A | 10/1990 | Trout | |
| 5,103,323 A | 4/1992 | Magarinos | |
| 5,412,439 A | 5/1995 | Horn | |
| 5,539,544 A | 7/1996 | Le Paih et al. | |
| 5,966,240 A | 10/1999 | Lange et al. | |
| 6,411,451 B1 | 6/2002 | Fliss et al. | |
| 7,683,310 B1 | 3/2010 | Sinclair et al. | |
| 9,958,583 B1 | 5/2018 | Brown | |
| 2005/0162575 A1 | 7/2005 | Harvie | |
| 2008/0186565 A1 | 8/2008 | Kreig-Kowald | |
| 2009/0268157 A1* | 10/2009 | Krieg-Kowald | A61F 9/022 351/159.63 |
| 2010/0128356 A1* | 5/2010 | Feklistov | G02B 5/0833 359/637 |
| 2010/0149483 A1 | 6/2010 | Chiavetta, III | |
| 2012/0008217 A1 | 1/2012 | Ishak et al. | |
| 2013/0215499 A1 | 8/2013 | Wang et al. | |
| 2014/0009827 A1 | 1/2014 | Simon et al. | |
| 2014/0293467 A1 | 10/2014 | Palikaras et al. | |
| 2015/0060652 A1 | 3/2015 | Volfson | |
| 2015/0268396 A1 | 9/2015 | Weber et al. | |
| 2015/0338683 A1 | 11/2015 | Perricone et al. | |

FOREIGN PATENT DOCUMENTS

| | | |
|---|---|---|
| JP | H055804 A | 1/1993 |
| WO | 19830004317 A1 | 12/1983 |
| WO | 2003060443 A1 | 7/2003 |
| WO | 20060073408 A2 | 7/2006 |
| WO | 2010068541 A1 | 6/2010 |
| WO | 2010077411 A1 | 7/2010 |
| WO | 20130054115 A1 | 4/2013 |
| WO | 20150179474 A1 | 11/2015 |
| WO | 20170163027 A1 | 9/2017 |
| WO | 20170163028 A1 | 9/2017 |
| WO | 20170163031 A1 | 9/2017 |
| WO | 20170163033 A1 | 9/2017 |

OTHER PUBLICATIONS

International Preliminary Report on Patentability for Appl No. PCT/GB2017/050754 dated Sep. 25, 2018, 8 pages.
International Preliminary Report on Patentability for Appl No. PCT/GB2017/050766 dated Sep. 25, 2018, 8 pages.
International Preliminary Report on Patentability for Appl No. PCT/GB2017/050741 dated Sep. 25, 2018, 8 pages.
PCT Search Report and Written Opinion for Appl No. PCT/GB2017/050741 dated May 23, 2017, 13 pages.
GB Search Report for Appl No. GB1604994.2 dated Sep. 26, 2016, 3 pages.
GB Search Report for Appl No. GB1619767.5 dated May 8, 2017, 7 pages.
GB Search Report for Appl No. GB1619763.4 dated May 3, 2017, 11 pages.
GB Search Report for Appl No. GB1604995.9 dated Sep. 26, 2016, 4 pages.
PCT Search Report and Written Opinion for Appl No. PCT/GB2017/050740 dated May 26, 2017, 14 pages.
GB Search Report for Appl No. GB1619764.2 dated May 3, 2017, 9 pages.
PCT Search Report and Written Opinion for Appl No. PCT/GB2017/050754 dated May 26, 2017, 13 pages.
GB Search Report for Appl No. GB1619765.9 dated May 9, 2017, 9 pages.
PCT Search Report and Written Opinion for Appl No. PCT/GB2017/050766 dated May 24, 2017, 13 pages.
Office Action dated May 18, 2020 for U.S. Appl. No. 16/087,116, 6 Pages.
Office Action dated Jun. 25, 2020 for U.S. Appl. No. 16/087,133, 31 Pages.
Notice of Allowance for U.S. Appl. No. 16/087,116, dated Jul. 29, 2020, 13 Pages.
Office Action for U.S. Appl. No. 16/087,124, dated Jul. 13, 2020, 28 Pages.

\* cited by examiner

Fig. 5

FILTER FOR LASER PROTECTION

RELATED APPLICATIONS

This application is a national phase application filed under 35 USC § 371 of PCT Application No. PCT/GB2017/050766 with an International filing date of Mar. 20, 2017, which claims priority of GB Patent Application 1604995.9 filed on Mar. 24, 2016 and GB Patent Application 1619765.9 filed on Nov. 23, 2016. Each of these applications is herein incorporated by reference in its entirety for all purposes.

FIELD OF THE INVENTION

The present invention relates generally to filters for laser protection and, additionally, to a method of forming such filters.

BACKGROUND OF THE INVENTION

It is known from, for example, US2014/0292467, to provide a generally transparent filter comprising a nanoparticle metamaterial structure such that a particular wavelength of electromagnetic radiation may be blocked. The use of such a filter at the windscreen (or windshield) of an aircraft, for example, protects against laser threats, which may otherwise damage pilot eyesight or temporarily dazzle the pilot. However, this method of forming laser protective/blocking films complex and costly, and typically only permits blocking of one or up to two laser wavelength bands. Furthermore, the film is generally rigid, and not easily conformable to a curved shape of a typical windscreen.

It is also known from, for example, US2014/0009827, to provide a generally transparent, conformable filter formed by holographic exposure of a photosensitive polymeric film by a plurality of coherent radiation sources for the purpose of forming eyeglasses for viewing stereoscopic images. However, there are a number of issues with the described method which make it unsuitable for forming laser protective/blocking filters of the type described above. Firstly, the bandwidth (or wavelength band) of blocked wavelengths is inevitably relatively high which means that the overall 'colour' of the resultant film is quite pronounced and the visible light transmission (%) is relatively low (indeed, can be as low as 15%). This is clearly undesirable, and in many cases entirely unacceptable, particularly for the application referenced above—it is self evident that the pilot must be able to see clearly through the aircraft vehicle.

SUMMARY

Aspects of the present invention seek to address at least some of these issues and, in accordance with a first aspect of the present invention, there is provided a method of forming a filter, comprising the steps of:
  selecting at least a first wavelength corresponding to a predetermined laser threat and having a first colour in the visible spectrum;
  providing a generally transparent substrate and forming a first notch filter region therein configured to substantially block incident radiation thereon of wavelengths within a first predetermined wavelength band including said first wavelength;
  selecting a second wavelength having a second colour in the visible spectrum and forming a colour balancing notch filter region in said substrate configured to block incident radiation thereon of wavelengths within a wavelength band including said second wavelength, thereby to balance or neutralise any colour distortion of said substrate caused by said first notch filter region.

Thus, by means of the claimed invention, any unwanted colour distortion of the substrate caused by formation of the first filter region can be neutralised, or at least 'balanced' or mitigated, by the formation of a second filter region centred around a wavelength of a different colour.

In an exemplary embodiment of the invention, each 'notch' filter region of a selected bandwidth (or wavelength band) and optical density can be formed using a process comprising holographic exposure of a photosensitive polymeric film. As a result, the filter regions can be formed very precisely to block a relatively very small bandwidth of radiation around, or including, a specifically selected wavelength. Thus, even if a number (e.g. three or more) of such notch filter regions are provided in the same polymeric film, the visible light transmission is retained at at least 70% because the 'notch' size (i.e. the bandwidth of blocked radiation) can be made so precisely and so small; and it is feasible, therefore, to use a plurality of additional colour balancing/neutralising filter regions to achieve an optimum result.

The film may be formed of a conformable, photosensitive polymer material, which may have a visible light transmission of at least 85% and/or a thickness of 1 to 100 micrometers.

In accordance with another aspect of the present invention, there is provided a conformable filter formed by the method substantially as described above.

The filter may additionally be configured to prevent transmission of radiation in a second predetermined wavelength band covering a selected second predetermined laser threat. In this case, of course, a further one or more colour neutralising/balancing notch filter regions may be incorporated to neutralise/balance any resultant, combined colour distortion caused by the principal (laser threat blocking) filter regions.

In an exemplary embodiment of the invention, the first predetermined wavelength band may cover or be centred on 532 nm. The second predetermined wavelength band may cover or be centred on 445 nm. In this case, the colour balancing notch filter region may cover or be centred on a selected wavelength in the red portion of the visible spectrum.

The filter may be additionally configured to prevent radiation in a third predetermined visible radiation band covering the wavelength of a third predetermined laser threat. In this case, the third predetermined visible wavelength band may cover or be centred on 650 nm, and one or more colour balancing notch filter regions may be provided centred around, or cover, wavelengths intermediate the selected wavelengths of predetermined laser threats.

More generally, the filter, thus formed, may be configured to prevent radiation from three or more predetermined wavelength bands, and incorporate one or more associated colour balancing notch filter regions to substantially neutralise the perceived colour of the filter.

In an exemplary embodiment, the filter may be comprised of a single layer of material adapted or configured for preventing the transmission of the predetermined visible wavelength band or bands, and incorporating any additional colour balancing/neutralising notch filter regions therein.

The bandwidth of at least one of the predetermined wavelength bands may be 10 nm, or less than 10 nm, e.g. 5 nm. However, the present invention is not necessarily intended to be limited in this regard.

Advantageously, the filter may have an optical density of at least 2 at the first predetermined wavelength band; and in one exemplary embodiment, the filter may have an optical density of at least 2 at each predetermined wavelength band. However, it will be appreciated that, at least in some cases, the optical density of the colour balancing/neutralising notch filter regions may be less than this, depending on the 'colour' of the blocked radiation, as the sensitivity of the human eye differs depending on the colour of visible radiation.

In one exemplary application, the filter may be provided as a conformal film for coupling to a window; and, in accordance with another aspect of the invention, there is provided a multi-layered window comprising a filter substantially as described above wherein the filter is interposed between layers of the window.

The present invention extends to a window for a vehicle, the window comprising a filter substantially as described above.

BRIEF DESCRIPTION OF THE DRAWINGS

These and other aspects of the present invention will be apparent from the following specific description, in which.

DETAILED DESCRIPTION

Figure 1:
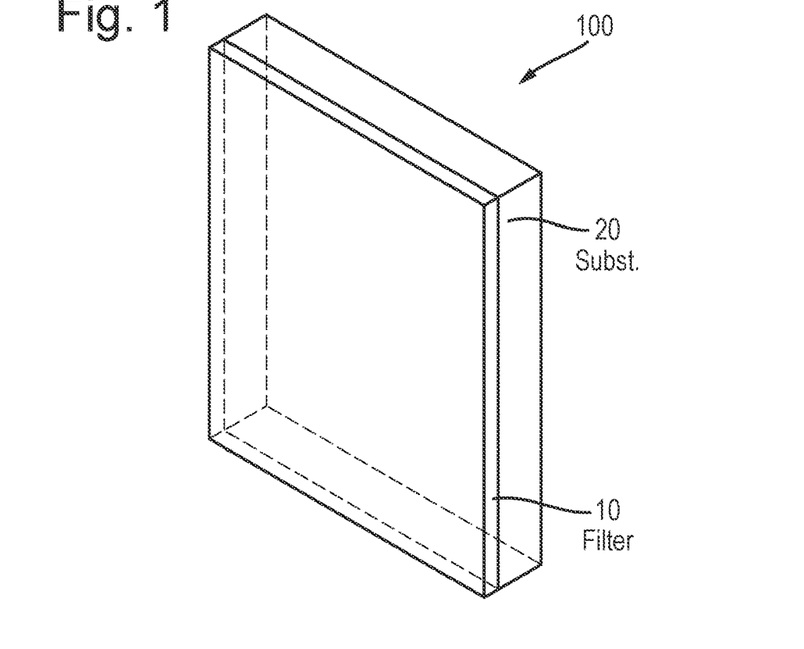
FIG. 1 is a schematic perspective view of a filter according to an exemplary embodiment of the present invention applied to a substrate.

With reference to FIG. 1, there is shown a layer of filter material 10 applied to a first face of a substrate 20 to provide a window 100 adapted for mitigating laser threats such as dazzle. The substrate 20 is substantially transmissive of visible light (for example, it may have a visible light transmission (VLT %) of around 90% of normally incident light) and may be formed, for example, from a glass or plastics material such as polycarbonate.

The filter material 10 is an interference filter formed by a method according to an exemplary embodiment of the present invention for holographically exposing a photosensitive film with a plurality of lasers having a set of predetermined wavelengths within a selected wavelength band of bandwidth, for example, 10 nm or less.

Conformable photosensitive (e.g. polymeric) films for use in exemplary embodiments of the present invention will be known to a person skilled in the art, and the present invention is not necessarily intended to be limited in this regard. Such photosensitive polymeric films are provided having varying degrees of inherent visible light transmission (VLT), ranging from less than 70% (and, possibly therefore, having a coloured tinge) up to 95% or more (and being substantially colourless and transparent). In respect of the present invention, suffice it to say that a photosensitive flexible/conformable (e.g. polymeric) film is selected having an inherent VLT of, for example, at least 85%. The film typically has a thickness of 1 to 100 micrometers. Thinner, currently known, films may not achieve useful optical densities. Indeed, in respect of currently known photosensitive polymeric films, the degree to which a selected radiation wavelength can be blocked (i.e. the effectiveness of a filter region formed therein) is determined by the thickness and refractive modulation index of the film and, also, by the optical design. Thus, the filter region thickness is ideally matched to the application and the potential power of the source from which protection is required (which may be dictated, at least to some extent, by the minimum distance from the target platform the laser threat may realistically be located and this, in turn, is dictated by application). In general, thicker films and films with higher refractive modulation indices would be selected if it were required to provide protection from higher power radiation sources or to provide greater angular coverage, but this might then have a detrimental effect on the inherent VLT of the film, so a balance is selected to meet the needs of a specific application.

Whilst the present detailed description makes specific reference to a vehicle window, it is to be understood that the principles and techniques disclosed hereinafter are equally applicable to other applications such as eyeglasses, contact lenses, sensor protection films, screens or pull-down visors, laser designators, etc. and the present invention is not necessarily intended to be limited in this regard. It will be understood by a person skilled in the art that the following principles and techniques can be readily adapted to different laser protective/blocking applications, simply by selection of the film and the specific wavelengths to which the film is exposed to form the filter region(s).

Figure 2:
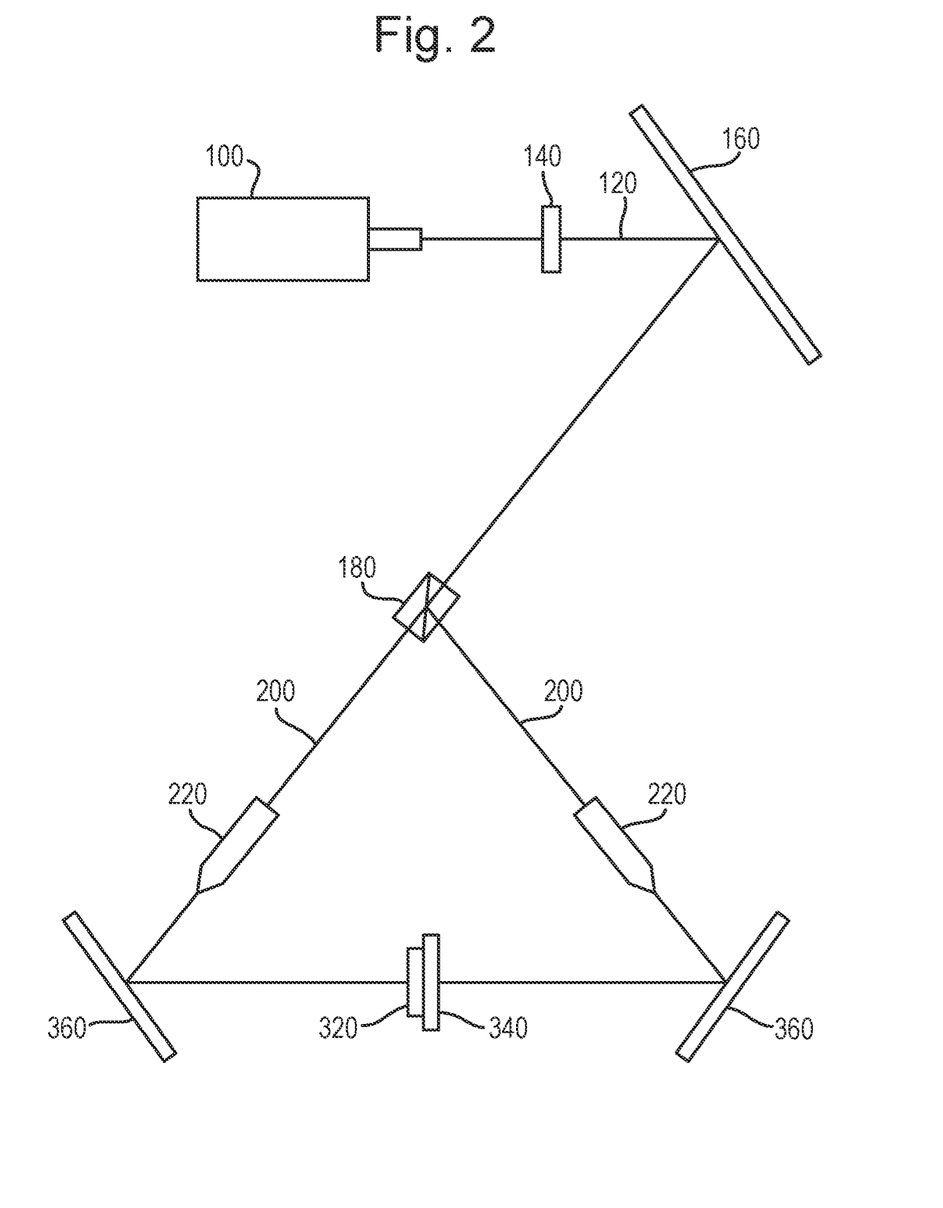
FIG. 2 is a schematic diagram illustrating a process of forming a filter region for use in a method according to an exemplary embodiment of the present invention.

Once the film has been selected, the required holographic exposure thereof is effected to form the filter regions of a required notch filter region to be provided thereon. Referring to FIG. 2 of the drawings, distinct filter regions defining a notch filter region of a predetermined bandwidth (e.g. 5 nm) may be formed by exposing the film to the intersection of two counter propagating laser beams for each of a set of laser wavelengths within the selected wavelength band defined by the selected wavelength and a spectral bandwidth including the selected wavelength. Each laser 100 (of a wavelength within the selected bandwidth) produces a laser beam 120 which is controlled by a shutter 140. The laser beam 120 is directed by a mirror 160 into a beam splitter 180 wherein the beam is divided into equal beam segments 200. Each beam segment 200 passes through a microscope objective 220 and is then reflected by a respective mirror 360 onto the photosensitive polymer film 320. Other optical devices (not shown) may be provided between the microscope objective 220 and the mirror 360 to, for example, focus or diverge the respective beam segment 200, as required. Furthermore, masking or other limiting techniques may be utilised to limit the extent or thickness to which the film is exposed to the beam segments 200, as will be understood by a person skilled in the art. As a specific (non limiting) example, if it is required to provide a notch filter region of bandwidth 5 nm around 520 nm, then a plurality of lasers 100 may be used to produce the notch filter region of (purely by way of example) 517.5 nm, 518 nm, 518.5 nm, 519 nm, 519.5 nm, 520 nm, 520.5 nm, 521 nm, 521.5 nm, 522 nm and 522.5 nm. The above-described exposure process may be performed consecutively for each of these laser wavelengths or, in some exemplary embodiments, the exposures may be performed substantially simultaneously. Other methods of forming a holographic filter region at each specified wavelength are known and could, alternatively, be used.

In many cases, and depending on the particular parameters applied and filter requirements of a specified application, the creation of one or more notch filter regions around respective predetermined wavelengths may result in some visible colour distortion of the film. For example, if a single notch filter region centred around a 'green' laser wavelength is created, then, depending on the composition of the film itself, its thickness and the bandwidth of the notch, there may be some resultant colour distortion of the filter which may, in some applications at least, be unacceptable; and aspects of the present invention provide a method of manufacturing a laser protective/blocking filter of the type described above, including process steps for neutralising or balancing such colour distortion.

Thus, and again using the above-mentioned example, consider the case where a notch filter region having an optical density of 2 is created in a conformable polymer film in the manner described above, having a central (blocked) wavelength of 520 nm and a bandwidth of 5 nm. This spectral bandwidth lies in the 'green' region of the visible spectrum, and may result in the filter appearing to have a yellow or brown tinged appearance. In order to counteract this and 'neutralise' the colour of the filter (such that it appears clear or at least less tinged to the eye), the inventors propose to incorporate one or more further notch filter regions in the film, using the process described above, designed to 'balance' the principal notch filter region and neutralise the colour/appearance of the filter. In this specific example, notch filter regions covering, respectively, 'red' and 'blue' regions of the visible spectrum may be formed in the film for this purpose. In some exemplary embodiments, the central (blocking) wavelength of each such additional notch filter region might be 'equally spaced' on either side of the central wavelength of the principal notch filter region. However, it is well known that the human eye is more sensitive to some colours than others, and the wavelength(s) of any additional, colour balancing notch filter regions would be dependent on the specific principal notch filter region(s) required to be neutralised. Furthermore, the optical density (OD) of such colour balancing notch filter regions would not necessarily need to be the same as that of the principal notch filter region for the same reason.

In other cases, it may not be possible or feasible to entirely neutralise any colour distortion resulting from a specified filter. This may particularly occur in the case where the filter is required to have two or more blocking wavelengths corresponding to respective predetermined laser threats. For example, a specific application may require a filter that blocks 520 nm (green) laser and 650 nm (red) laser, and a filter incorporating two associated notch filter regions is created accordingly. The resultant colour distortion can still be balanced, if not completely neutralised, by incorporating a further, 'blue' notch filter region centred at a selected wavelength and having a selected bandwidth and optical density dependent on the specific characteristics of the principal notch filter regions.

It will be apparent to a person skilled in the art that the calculation of the wavelength at which any balancing/neutralising notch filter regions are best centred, as well as their required bandwidth and optical density, can be determined in accordance with known principles of photoreception of the human eye, and may incorporate reference to the standard luminosity function or 'eye sensitivity' associated with the colour(s) of the principal notch filter region(s). Thus, the specific characteristics required for the or each colour balancing/neutralising notch filter region can be calculated in accordance with the standard luminosity function of the human eye in relation to the wavelength(s) of the principal notch filter region(s) to achieve the best visual result.

Once the exposure process has been completed, the resultant hologram can be fixed by, for example, a bleaching process.

Figure 3:
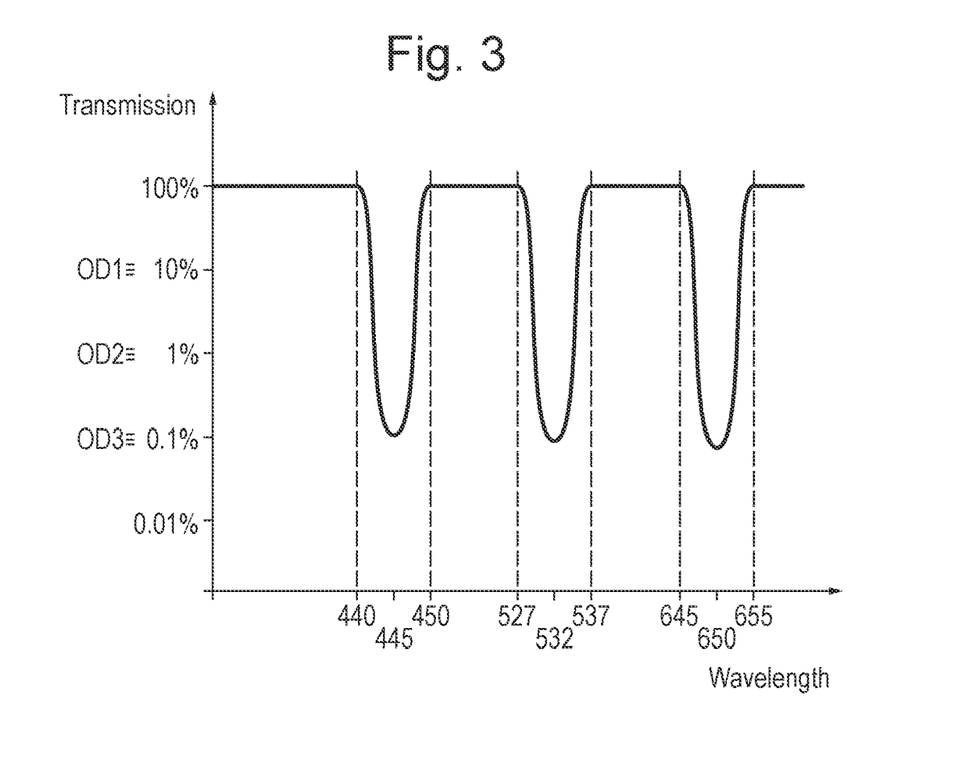
FIG. 3 is a schematic perspective view of the filter of FIG. 1 configured to detect radiation.

The transmission characteristic (which may alternatively be referred to as the transfer function) of visible electromagnetic radiation incident on the filter 10 is illustrated in FIG. 3. The transmission intensity relative to incident radiation intensity is shown on the y-axis and the wavelength of the incident radiation is shown on the x-axis.

As can be seen on the plot, across the range of wavelengths the intensity of the transmitted radiation is close to 100% of that which is incident. In general a VLT % of 90% would be acceptable if 100% was not feasible.

There are three distinct notches in the illustrated transmission characteristic associated with three wavelength bands. These are in particular a 10 nm band centred on 455 nm, a 10 nm band centred on 532 nm and a 10 nm band centred on 650 nm. In an exemplary embodiment, the 532 nm band may have been selected to block an associated predetermined laser threat, whereas the 455 nm and 650 nm bands may have been incorporated to neutralise the colour distortion resulting from the 532 nm notch filter region. In general any number of notches from the group consisting of 405 nm, 455 nm, 520 nm, 532 nm, and 650 nm may be selected to block corresponding predetermined laser threats. Indeed, notches may be chosen to coincide with any expected laser threat wavelength, and additional, colour balancing notch filter regions may be selected and incorporated accordingly. Still further, the bandwidth of each notch filter region may be 5 nm.

At the centre of each of these bands, the intensity of the transmitted radiation is at a minimum and has an optical density of approximately 3, which is equivalent to 0.1% of the initially incident radiation.

Figure 4:
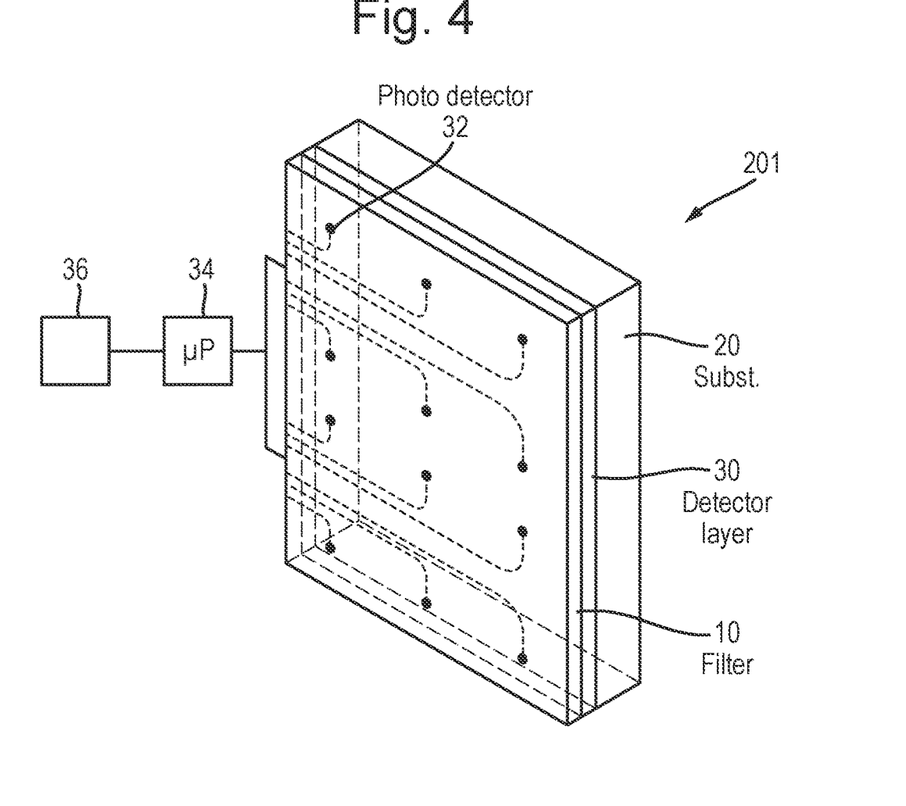
FIG. 4 is a graph in which the transmission characteristic of the filter of FIG. 1 is plotted.

With reference to FIG. 4 there is shown generally at 201 a window. The window 200 comprises a transparent substrate 20 a first face of which has been coupled a radiation detector in the form of a detector layer 30.

Coupled to the opposite face of the detector layer 30 there is provided a layer of the holographic filter material 10.

As such the substrate 20, detector layer 30 and filter material 10 can be considered as a stacked multi-layer structure.

The detector layer 30 comprises an array of photodetectors 32 distributed so as to extend substantially across the window 200. The photodetectors 32 are sufficiently small to be substantially invisible to the casual observer (though in practice there may be some reduction on the VLT %). Each photodetector is electrically connected to a processor module 34. In some embodiments, including the present one, each photodetector is uniquely connected to a unique port on the processor module 34.

The processor module 34 is in turn connected to an alert module 36.

Figure 5:
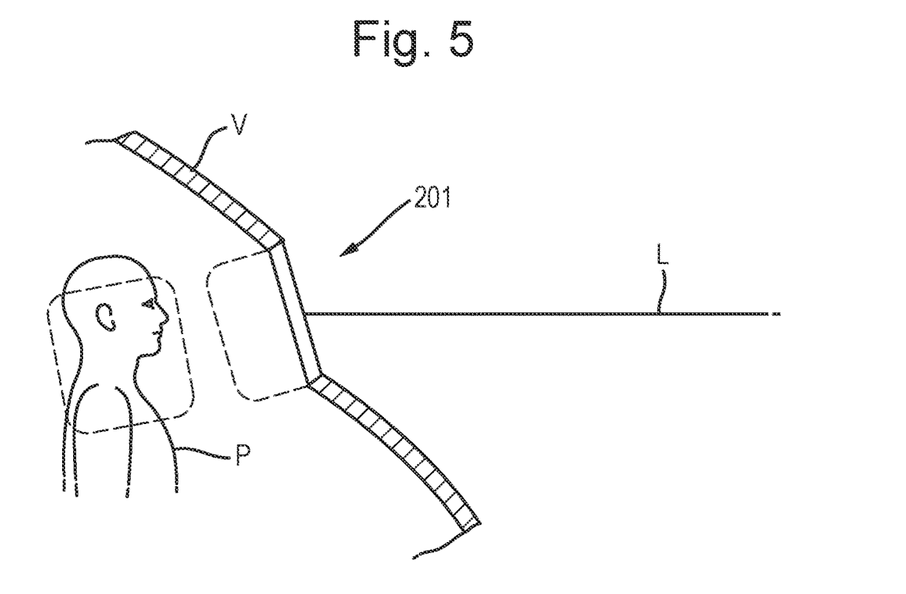
FIG. 5 illustrates schematically the filter of FIG. 1 implemented on the windscreen of a vehicle.

FIG. 5 shows a window 201 as shown in FIG. 4 deployed as a windscreen on a vehicle V, which in this example is an aircraft. A pilot P is positioned behind the windscreen and a laser beam L, having a wavelength of 532 nm, is shown pointing at the windscreen. Laser beam L will have some degree of divergence as the beam propagates through the atmosphere, which will result in a certain 'spot size' observed at the windscreen.

In operation the window 201 may be used to mitigate the effects of the laser beam L, and alert the pilot to the existence of the laser threat.

In particular, as the laser beam L propagates onto the window 201 it will pass through the substrate 20 and into the detector layer 30 where some laser light will fall on one or more of the photodetectors 32 (depending on spot size).

The laser light subsequently propagates from the detector layer 30 and on the filter 10 where the light becomes substantially attenuated. Assuming the filter 10 to have the transmission characteristics shown in FIG. 3 and the laser beam L to be a green laser of 532 nm, the laser beam L will be attenuated to 0.1% of its original intensity.

Accordingly, the pilot P is able to look out of the windscreen with a reduced chance of the laser beam L harming his or her sight, or distracting him or her from flying the plane safely.

Meanwhile, the laser light having fallen on certain photodetectors 32, an electrical signal is generated at each illuminated detector 32 and sent to the processing unit 34. At the processing unit 34 the electrical signals received from the illuminated photodetectors 32 are analysed to confirm or deny the detection of a laser beam. In this case, the processing module 36 generates a signal confirming the presence of the laser beam and relays this to the alert module 36.

Each photodetector 32 can have a unique location at the filter, registered with the processor module such that signals from each photodetector 32 can be correlated with a certain location at the filter. Further this location can be correlated with a particular point on the window provided the relationship between the window and the filter is registered at the processing module. Thus the processing module can determine, from detecting which photodetectors are illuminated, not only the presence of a threat but also the general dimensions of the 'spot' and where on the window the illumination is occurring. Some information relating to the source of the threat can be derived from such measurements. If embodiments are provided with layers of photodetectors, it may be possible to establish more confident estimates of the threat location.

In the present embodiment the photodetectors 32 are configured for detecting radiation at the predetermined wavelength or predetermined wavelengths. For example the photodetector 32 could be configured to send a signal only if 527-537 nm radiation illuminated it. As such the system needs less noise-rejection provisions and/or can provide fewer false positive signals.

Upon receiving the signal confirming the presence of the laser beam, the alert module issues an alert to notify the pilot P (or another operator) of the laser beam. Such alert could be a visual alert (for instance on an instrument in the cockpit) and/or an audible alert. Such alert could be a signal sent (e.g. by an RF transmitter within the alert module) to a further aircraft or a further element of aerospace infrastructure such as an Air Traffic Control base.

Accordingly, should the pilot be otherwise unaware of the laser beam (for instance because it is sufficiently attenuated by the filter 10 to be negligible within the vehicle) the alert will inform as to the existence of the threat and further action (reporting to ground based security personnel, warning other aircraft) can be taken to address or remove the threat.

As an alternative to window 200, the window 100 may be provided as the windscreen in vehicle V. Here there is no detection layer 30 and so there can be no automatic alert or detection of the laser threat.

Nonetheless the holographic filter 10 will function to attenuate the intensity of the laser beam L and thereby protect the pilot.

The above discussion has provided an overview of how the present invention may mitigate the threat of laser beams in various applications.

Presently various lasers are commercially available which could be used against a number of targets at a number of different stand-off ranges. The likely distance and the power of the laser determine how effective the filter needs to be in order to prevent injury to the onlooker. An intensity-at-eyeball of 0.001 W/cm$^2$ or less should be sufficient to prevent eye damage.

Table 1 shows, for a 3 W laser with 0.5 mrad beam divergence and no atmospheric loss at various stand-off distances, the calculated minimum optical densities (OD) such that damage to the eye can be avoided by blinking (i.e. damage is negligible at this OD unless exposure is greater than 0.5 s, which is a determined minimum multiplied by a factor of safety of 2), and such that there is enough protection to render negligible the risk of damage from a 10 second exposure. Accordingly suggested ranges for ODs are proposed.

TABLE 1

| Distance (m) | Beam diameter (mm) | 'Spot' Size (mm$^2$) | Intensity (W/Cm$^2$) | Typical Application | min OD for 0.5 s exposure | min OD for 10 s exposure | Example OD ranges (to nearest 0.5) |
|---|---|---|---|---|---|---|---|
| 0 | 3 | 7.1 | 42.4 | n/a | 4.03 | 4.63 | 4.5-6.0 |
| 5 | 6 | 23.8 | 12.6 | Car/train/bus | 3.50 | 4.10 | 3.5-5.5 |
| 10 | 8 | 50.3 | 6.0 | Car/train/bus | 3.18 | 3.78 | 3.5-5.5 |
| 50 | 28 | 615.8 | 0.5 | Car/train/bus/aircraft | 2.10 | 2.70 | 2.5-4.0 |
| 100 | 53 | 2206.2 | 0.1 | Car/train/bus/aircraft | 1.40 | 2.00 | 1.5-3.5 |
| 500 | 253 | 50272.6 | 0.006 | Aircraft | 0.18 | 0.78 | 0.5-2.5 |
| 1000 | 503 | 198712.8 | 0.002 | Aircraft | n/a | 0.30 | 0-1.5 |

Table 2 shows, for a 1 W laser with 1.2 mrad beam divergence and no atmospheric loss at various stand-off distances, the calculated minimum optical densities (OD) such that damage to the eye can be avoided by blinking (i.e. damage is negligible at this OD unless exposure is greater than 0.5 s, which is a determined minimum multiplied by a factor of safety of 2), and such that there is enough protection to render negligible the risk of damage from a 10 second exposure. Accordingly suggested ranges for ODs are proposed.

TABLE 2

| Distance (m) | Beam diameter (mm) | 'Spot' size (mm2) | Intensity (W/Cm2) | Typical application | min OD for 0.5 s exposure | min OD for 10 s exposure | Example OD ranges (to nearest 0.5) |
|---|---|---|---|---|---|---|---|
| 0 | 3 | 7.1 | 14.1 | n/a | 3.55 | 4.15 | 4.0-5.5 |
| 5 | 9 | 63.6 | 1.57 | Car/train/bus | 2.59 | 3.20 | 3.0-4.5 |
| 10 | 15 | 176.7 | 0.57 | Car/train/bus | 2.15 | 2.76 | 2.5-4.5 |
| 50 | 63 | 3117.3 | 0.03 | Car/train/bus/aircraft | 0.88 | 1.48 | 1.0-3.0 |
| 100 | 123 | 11882.3 | 0.008 | Car/train/bus/aircraft | 0.30 | 0.90 | 0.5-2.5 |
| 500 | 603 | 285577.8 | 0.0004 | Aircraft | n/a | n/a | 0.5-1.5 |
| 1000 | 1203 | 1136635.3 | 0.00009 | Aircraft | n/a | n/a | n/a |

These experiments show that an optical density of 2 would tend to provide sufficient attenuation for aerospace applications, where attackers would struggle to get within 100 m of the aircraft.

So that the dazzle can be prevented (dazzle being where the vision of the operator is temporarily impaired by the laser light but not permanently damaged) the OD values given in Table 1 or Table 2 should be increase in each scenario by 1, or more preferably 1.5 (i.e. and OD of 1 should become and OD of 2 or 2.5 to prevent dazzle).

In a variant of the radiation detector shown in FIG. 2, the radiation detector may have the form of a patch arranged in the plane of the filter, or in other words at or near a boundary of the filter. Said patch could comprise an localised photo-detector or array thereof and would be interfaced with the processor module and alert module in an equivalent manner. This approach would be suited to contexts where the spot size of the laser was sufficiently large to illuminate the periphery of the window, so that the patch need not be positioned in the operator's view.

In a variant of the window and substrate arrangement of FIG. 1, the window may be comprised by a number of laminar substrates between which could be positioned the filter 10.

In a variant of the window and substrate arrangement of FIG. 2, the window may be comprised by a number of laminar substrates between which could be positioned the filter and detector.

It will be apparent to a person skilled in the art, from the foregoing description, that modifications and variations can be made to the described embodiments without departing from the scope of the invention as defined by the appended claims.

What is claimed is:

1. A method of forming a single layer holographic film filter, comprising the steps of:
   selecting at least a first wavelength corresponding to a predetermined laser threat and having a first colour in the visible spectrum;
   providing a generally transparent substrate and forming a first notch filter region thereon configured to substantially block incident radiation thereon of wavelengths within a first predetermined wavelength band including said first wavelength;
   selecting a second wavelength having a second colour in the visible spectrum and forming a colour balancing notch filter region in said substrate configured to block incident radiation thereon of wavelengths within a wavelength band including said second wavelength, thereby to balance or neutralise any colour distortion of said substrate caused by said first notch filter region;
   wherein the filter is comprised of a single layer of material adapted or configured for preventing the transmission of the predetermined visible wavelength band or bands, wherein said filter regions are formed by holographic exposure of said single layer holographic film to radiation of wavelengths within said wavelength bands.

2. The method according to claim 1, wherein said colour balancing notch filter region is formed of a photosensitive polymer material.

3. The method according to claim 2, wherein said film has a visible light transmission of at least 85%.

4. A conformable holographic film filter formed by:
   selecting at least a first wavelength corresponding to a predetermined laser threat and having a first colour in the visible spectrum;
   providing a generally transparent substrate and forming a first notch filter region therein configured to substantially block incident radiation thereon of wavelengths within a first predetermined wavelength band including said first wavelength;
   selecting a second wavelength having a second colour in the visible spectrum and forming a colour balancing notch filter region in said substrate configured to block incident radiation thereon of wavelengths within a wavelength band including said second wavelength, thereby to balance or neutralise any colour distortion of said substrate caused by said first notch filter region;
   wherein the filter is comprised of a single layer of material adapted or configured for preventing the transmission of the predetermined visible wavelength band or bands.

5. The conformable filter according to claim 4, additionally configured to prevent transmission of radiation in a second predetermined wavelength band covering a selected second predetermined laser threat.

6. The filter according to claim 5 wherein the second predetermined wavelength band covers or is centred on 445 nm, and an associated colour balancing notch filter region is centred on a wavelength within the red and/or green region(s) of the visible spectrum.

7. The filter according to claim 4, wherein the first predetermined wavelength band covers or is centred on 532 nm, and an associated colour balancing notch filter region is centred on a wavelength within the red and/or blue region(s) of the visible spectrum.

8. The filter according to claim 4, wherein the filter is additionally configured to prevent radiation in a third predetermined wavelength band covering the wavelength of a third predetermined laser threat, and optionally wherein the third predetermined visible wavelength band covers or is centred on 650 nm.

9. The filter according to claim 4, wherein the bandwidth of at least one of the predetermined wavelength bands is between 5 and 10 nm.

10. The filter according to claim 4, wherein the filter has an optical density of at least 2 at the first and/or each predetermined wavelength band.

11. The filter according to claim 4, wherein the filter is provided as a conformal film for coupling to a window.

12. A multi-layered window comprising a filter according to claim 4, wherein the filter is interposed between layers of the window.

13. A window for a vehicle, the window comprising a filter according to claim 4.

14. A conformal single layer film filter formed by:
- selecting at least a first wavelength corresponding to a predetermined laser threat and having a first colour in the visible spectrum;
- providing a generally transparent substrate and forming a first notch filter region therein configured to substantially block incident radiation thereon of wavelengths within a first predetermined wavelength band including said first wavelength, the first predetermined wavelength band covers or is centred on 532 nm, and an associated colour balancing notch filter region is centred on a wavelength within the red and/or blue region(s) of the visible spectrum;
- selecting a second wavelength having a second colour in the visible spectrum and forming a colour balancing notch filter region in said substrate configured to block incident radiation thereon of wavelengths within a wavelength band including said second wavelength, thereby to balance or neutralise any colour distortion of said substrate caused by said first notch filter region, the second predetermined wavelength band covers or is centred on 445 nm, and an associated colour balancing notch filter region is centred on a wavelength within the red and/or green region(s) of the visible spectrum;
- the filter is additionally configured to prevent radiation in a third predetermined wavelength band covering the wavelength of a third predetermined laser threat, and optionally wherein the third predetermined visible wavelength band covers or is centred on 650 nm;
- wherein the bandwidth of at least one of the predetermined wavelength bands is between 5 and 10 nm;
- wherein the conformal film is formed of a photosensitive polymer material and has a visible light transmission of at least 85%;
- the filter regions are formed by holographic exposure of the film to radiation of wavelengths within the wavelength bands;
- wherein the filter is comprised of a single layer of material adapted or configured for preventing the transmission of the predetermined visible wavelength band or bands, having an optical density of at least 2 at the first and/or each predetermined wavelength band;
- wherein the filter is provided as a conformal film for coupling to a window.

* * * * *